US012071647B2

(12) United States Patent
Liang et al.

(10) Patent No.: US 12,071,647 B2
(45) Date of Patent: Aug. 27, 2024

(54) ***MORTIERELLAALPINA* STRAIN AND USE THEREOF, MICROBIAL OIL CONTAINING ARA AT SN-2 POSITION AND PREPARATION AND USES THEREOF**

(71) Applicant: Hanpeng Qu, Hunan (CN)

(72) Inventors: Yun Liang, Hunan (CN); Sheng Cao, Hunan (CN); Shenjian Wang, Hunan (CN)

(73) Assignee: Hanpeng Qu, Changsha (CN)

( * ) Notice: Subject to any disclaimer, the term of this patent is extended or adjusted under 35 U.S.C. 154(b) by 0 days.

(21) Appl. No.: 17/375,214

(22) Filed: Jul. 14, 2021

(65) Prior Publication Data

US 2021/0340582 A1 Nov. 4, 2021

Related U.S. Application Data

(63) Continuation of application No. PCT/CN2020/130378, filed on Nov. 20, 2020.

(30) Foreign Application Priority Data

Nov. 26, 2019 (CN) ........................ 201911175789.3

(51) Int. Cl.

| | |
|---|---|
| ***C12P 7/64*** | (2022.01) |
| ***A23D 9/04*** | (2006.01) |
| ***A23L 33/00*** | (2016.01) |
| ***A23L 33/115*** | (2016.01) |
| ***C12N 1/14*** | (2006.01) |
| ***C12P 7/6463*** | (2022.01) |
| ***C12P 7/6472*** | (2022.01) |
| *C12R 1/645* | (2006.01) |

(52) U.S. Cl.

CPC .............. *C12P 7/6463* (2013.01); *A23D 9/04* (2013.01); *A23L 33/115* (2016.08); *A23L 33/40* (2016.08); *C12N 1/145* (2021.05); *C12P 7/6472* (2013.01); *A23V 2002/00* (2013.01); *C12R 2001/645* (2021.05)

(58) Field of Classification Search

CPC ..... C12P 7/6463; C12P 7/6472; A23L 33/115; A23L 33/40; C12N 1/145; A23D 9/04; C12R 2001/645; A23V 2002/00

USPC ........................................................ 426/601

See application file for complete search history.

(56) References Cited

U.S. PATENT DOCUMENTS 5,658,767 A * 8/1997 Kyle ..................... A23C 11/04 426/585
2018/0064138 A1 3/2018 Apt et al.

FOREIGN PATENT DOCUMENTS

| | | | |
|---|---|---|---|
| CN | 103695483 | A | 4/2014 |
| CN | 107581615 | A | 1/2018 |
| CN | 108517338 | A | 9/2018 |
| CN | 108823109 | A | 11/2018 |
| CN | 110438173 | A | 11/2019 |
| CN | 111378701 | A | 7/2020 |
| EP | 2653040 | A1 | 10/2013 |
| WO | 2015058115 | A1 | 4/2015 |

OTHER PUBLICATIONS

Liu,Bo et al. "Progress on microbial glyceride biosynthesisand metabolic regulation in oleaginous microorganisms." Acta Microbiologica Sinica, vol. 45 No. 1, Feb. 28, 2005, p. 153-156.
Tang,Wenjia. "Enzymatic synthesis of monoacylglycerols and symmetrical triacylglycerols rich in arachidonic acid at the sn-2 position." Chinese Master's Theses Full-text Database, Engineering Science I, Dec. 31, 2016, abstract, p. 5, p. 32 tables 3-8.
Li,Xia. "Optimization, of fermentatation, conditions for arachidonic acid production wim mortierella alpina." China Brewing, vol. 34 Number 5, Dec. 31, 2015, abstract, p. 5, p. 52-55.
Wu, Wenjia et al. "Lipid characterization ofan arachidonic acid-rich oil producing fungus *Mortierella alpina.*" Chinese Journal ofChemical Engineering, No. 23, Dec. 31, 2015, p. 1183-1187.

* cited by examiner

*Primary Examiner* — Brent T O'Hern

(57) ABSTRACT

This disclosure relates to microbial technology, and more particularly to a *Mortierellaalpina* strain and a use thereof, a microbial oil containing ARA at an Sn-2 position, a preparation and uses thereof. Sn-2 fatty acids of the triglyceride in the microbial oil include 23% or more by weight of ARA. The microbial oil is prepared by fermentation using *Mortierellaalpina* strain GDMCC No. 607344.

5 Claims, No Drawings

*MORTIERELLAALPINA* STRAIN AND USE THEREOF, MICROBIAL OIL CONTAINING ARA AT SN-2 POSITION AND PREPARATION AND USES THEREOF

CROSS-REFERENCE TO RELATED APPLICATIONS

This application is a continuation of International Patent Application No. PCT/CN2020/130378, filed on Nov. 20, 2020, which claims the benefit of priority from Chinese Patent Application No. 201911175789.3, filed on Nov. 26, 2019. The content of the aforementioned application, including any intervening amendments thereto, is incorporated herein by reference in its entirety.

TECHNICAL FIELD

The present disclosure relates to microbial technology, and more particularly to a *Mortierellaalpina* strain and a use thereof, a microbial oil containing arachidonic acid (ARA) at an Sn-2 position, and a preparation and uses thereof.

BACKGROUND

Lipids, as essential nutrients for human body, act as indispensable raw materials for building cells and tissues and supply energy for body, and they can also act as a carrier for the fat-soluble vitamins. However, before exerting their biological and physiological effects, lipids need to be digested and absorbed in the intestines first. Lipases from the pancreas and small intestines and cholate in the bile participate in the digestion and absorption of the lipids under an alkaline environment formed by bicarbonate secreted from the pancreas and bile. The lipid absorption efficiency greatly depends on the enzymes involved in the digestion and the action mechanisms thereof, and the structures of the lipid. A large number of studies have shown that the structures of the lipid largely influence the absorption rate of lipid in human body. With regard to the triglyceride, the fatty acids are classified into Sn-1, Sn-2 and Sn-3 position fatty acids according to their positions on the glycerol skeleton. Pancreatic lipase, as a primary lipase enzyme, attaches to a water-oil interface to hydrolyze dietary fat molecules. Meanwhile, the pancreatic lipase specifically catalyzes the hydrolysis of ester bonds at the Sn-1 and Sn-3 positions. As a consequence, under the catalysis of the pancreatic lipase, the triglyceride structure is converted into free fatty acids and a monoglyceride. In the conversion, the free fatty acids are from the fatty acids at the Sn-1 and Sn-3 positions and, have difficulty in penetrating into bile salt micelle to be absorbed, such that they will combine with calcium and magnesium ions in the intestine to form insoluble soap salts to be wasted, whereas the monoglyceride formed from the fatty acid at the Sn-2 position is easy to penetrate into bile salt micelle to be absorbed. Therefore, the absorption rate of fatty acids at the Sn-2 position in human body is higher than that of the fatty acids at the Sn-1 and Sn-3 positions.

As consumers become more aware of the health impact of fatty acids, microbial oils, as primary resources of polyunsaturated fatty acids, have been largely adopted in the production of infant food and nutraceuticals, and their nutritional benefits are increasingly recognized by public. In addition, people are more and more concerned about the absorption rate of functional polyunsaturated fatty acids such as arachidonic acid (ARA) and docosahexaenoic acid (DHA). 90% of fatty acids in microbial oils exist in the form of triglyceride; however, in the existing microbial oils, the fatty acids at the Sn-2 position of triglyceride are far less than those at the Sn-1 and Sn-3 positions. Most of Sn-1 and Sn-3 fatty acids are formed into soap salts and wasted, which decreases the benefits of the microbial oils.

SUMMARY

The object of the present disclosure is to provide a *Mortierellaalpina* strain and a use thereof, a microbial oil containing arachidonic acid (ARA) at an Sn-2 position, and a preparation and uses thereof, to solve the problem that in the existing microbial oils, ARA is mainly incorporated at Sn-1 and Sn-3 positions of triglyceride, leading to poor absorption rate of ARA in human body.

The microbial oil provided herein is produced by fermentation using *Mortierellaalpina*, and Sn-2 fatty acids of the triglyceride in the microbial oil includes 23% or more by weight of the ARA, improving the absorption of ARA.

In order to realize the above-mentioned object, in a first aspect, the present disclosure provides a microbial oil, comprising:

a triglyceride;

wherein Sn-2 fatty acids of the triglyceride comprise 23% or more by weight of ARA.

In some embodiments, a weight percentage of ARA in the microbial oil is not less than 38%.

In a second aspect, the present disclosure further provides a method for producing a microbial oil, comprising:

inoculating a *Mortierellaalpina* strain into a fermentation medium for fermentation to produce the microbial oil;

wherein the *Mortierellaalpina* strain has an accession number of GDMCC No. 60734.

In a third aspect, the present disclosure provides a microbial oil produced by the above-mentioned method, wherein the microbial oil comprises a triglyceride; and Sn-2 fatty acids of the triglyceride comprise 23% or more by weight of ARA.

In a fourth aspect, the present disclosure provides a food comprising the above-mentioned microbial oil, wherein the food is an infant formula food, a nutraceutical or a health food.

In a fifth aspect, the present disclosure provides a *Mortierellaalpina* strain, wherein the *Mortierellaalpina* strain has an accession number of GDMCC No. 60734.

In a sixth aspect, the present disclosure provides an application of the above-mentioned *Mortierellaalpina* strain in the production of a microbial oil.

The microbial oil produced by the fermentation using *Mortierellaalpina* is rich in ARA, and a weight percentage of the Sn-2 ARA of the triglyceride in the microbial oil is not less than 23%, preferably 30%, which effectively facilitates the absorption and utilization of ARA in the microbial oil.

The features and beneficial effects will be further described in detail below with reference to the embodiments.

Deposit of Microorganisms

The *Mortierellaalpina* strain of the present disclosure has been deposited in Guangdong Microbial Culture Collection Center (GDMCC, Guangdong Institute of Microbiology, $5^{th}$ Floor, No. 59 Building, No. 100 Xianliezhong Road, Guangzhou, 510070, China) on Aug. 8, 2019 with an accession number of GDMCC No. 60734.

DETAILED DESCRIPTION OF EMBODIMENTS

It should be noted that endpoints and values within ranges disclosed herein are only exemplary, and are intended to include any values close to these values and ranges. Any possible combination of numerical values within the range to form one or more new ranges should be considered to be expressly disclosed in this disclosure.

In a first aspect, the present disclosure provides a microbial oil, where the microbial oil includes a triglyceride, and Sn-2 fatty acids of the triglyceride contain 23% or more by weight of ARA.

In some embodiments, the Sn-2 fatty acids of the triglyceride contain 30%, preferably 31%, or more by weight of ARA.

The ARA is an abbreviation of arachidonic acid.

In some embodiments, the microbial oil includes 90% or more by weight of the triglyceride.

In some embodiments, a weight percentage of ARA in the microbial oil is not less than 38%.

It should be understood that the total ARA is a total amount of ARA in the microbial oil, and is measured according the method of GB 26401-2011. Triglyceride ARA refers to the ARA incorporated to the glycerol skeleton through ester bonds.

In some embodiments, a weight percentage of the Sn-2 ARA of the triglyceride in the microbial oil is not less than 23%.

In some embodiments, a weight percentage of ARA at the Sn-2 position of the triglyceride is not less than 23%, and a weight percentage of the triglyceride ARA in the microbial oil is not less than 38%.

In a second aspect, the present disclosure further provides a method for producing a microbial oil, including:

inoculating a *Mortierellaalpina* strain into a fermentation medium for fermentation to produce the microbial oil;

where the *Mortierellaalpina* strain has an accession number of GDMCC No. 60734.

The strain can be obtained by a method conventionally used in the art.

The *Mortierellaalpina* GDMCC No. 60734 provided herein is obtained by screening after mutagenesis.

The mutagenesis is performed according to a conventional method, such as physical mutagenesis (ultraviolet mutagenesis, atmospheric room temperature plasma (ARTP) mutagenesis) and chemical mutagenesis.

In some embodiments, the mutagenesis is performed by ARTP mutagenesis.

The ARTP mutagenesis is carried out using a conventional mutagenesis system such as multifunctional mutagenesis system (MPMS) produced by Adhoc Interteck Co., Ltd. (Beijing, China).

The mutagenesis is performed according to conventional operations in the art. In an embodiment, the mutagenesis is performed at a plasma mutagenesis power of 80-120 W, a gas flow rate of 8-12 SLM (standard liter per minute) and a treatment distance of 1-3 mm.

The mutagenesis time is 1-6 min, preferably 180-210 s.

In some embodiments, a lethality of the *Mortierellaalpina* strain is 90-95% through the above-mentioned operations.

The mutagenesis can be performed on spores of a starting strain, and the spores can be provided in the form of a spore suspension. In some embodiments, the spore suspension is prepared through steps of: activating a starting strain on a slant medium to obtain the spores; and dispersing the spores in sterile water to prepare the spore suspension. Preferably, a concentration of the spore suspension is $10^6$-$10^8$ spores/mL.

After the strains obtained from the mutagenesis are subjected to multiple screenings to obtain a strain with high yield of Sn-2 ARA.

It should be understood by those skilled in the art that the percentage of the triglyceride with ARA at the Sn-2 position is used as an indicator for the screening of a desired high yield strain.

The content of Sn-2 fatty acids is detected according to the method recited in GB/T 24984-2010/ISO 6800:1997 "Animal and Vegetable Fats and Oils-Determination of the Composition of Fatty Acids in the 2-position of the Triglyceride Molecules".

In order to obtain a strain with high stability, the strains obtained by screening can also be evaluated for genetic stability. It has been widely accepted in the verification of genetic stability in the modern breeding that if the strain obtained from the mutation breeding can still meet the expected requirements of biological characteristics after five passages, it is considered to have high stability.

Through the mutagenesis, screening and genetic stability evaluation mentioned above, a strain with high yield of Sn-2 ARA is obtained.

The *Mortierellaalpina* strain of the present disclosure has been deposited in Guangdong Microbial Culture Collection Center (GDMCC, Guangdong Institute of Microbiology, 5th Floor, No. 59 Building, No. 100 Xianliezhong Road, Guangzhou, 510070, China) on Aug. 8, 2019 with an accession number of GDMCC No. 60734.

An Sn-2 ARA-rich microbial oil is produced by the fermentation using the *Mortierellaalpina* strain, and the fermentation method has no special requirements as long as it enables the proliferation of the *Mortierellaalpina* strain.

There are no special requirements for the fermentation by the *Mortierellaalpina* strain. In some embodiments, the fermentation is performed at 27-31° C. for 4-8 days under a ventilation rate of 0.5-1.1 vvm.

When the *Mortierellaalpina* strain is inoculated in the form of a seed liquid, the inoculation amount can be selected in a wide range, such as 5-10% (v/v).

The fermentation medium used herein can be a medium commonly used in the art for the fermentation by the *Mortierellaalpina*. The fermentation medium includes a carbon source and a nitrogen source.

The carbon source is glucose, sucrose, starch or other substances that can provide a carbon source or a combination thereof, and the nitrogen source is peptone, yeast powder, corn steep liquor powder or other substances that can provide a nitrogen source or a combination thereof.

Preferably, the carbon source is selected from the group consisting of glucose, starch, sucrose and a combination thereof, and the nitrogen source is selected from the group consisting of peptone, yeast powder, yeast extract, corn steep liquor powder and a combination thereof.

The carbon-to-nitrogen ratio can be selected in a wide range. Preferably, the carbon-to-nitrogen ratio is (3-18):1.

During the fermentation, the nitrogen source is added into the fermentation medium at one time, and beside the initial addition, the carbon source can be continuously supplied to adjust the carbon-to-nitrogen ratio. When approaching the fermentation end, the carbon source is not supplied into the medium any more so that the residual sugar is reduced to 0. In this way, an auxotrophic condition is created by adjusting the carbon-to-nitrogen ratio to improve the oil production of the *Mortierellaalpina* strain.

In order to increase a yield of the fermentation product, in some embodiments, the method further includes: activating the *Mortierellaalpina* strain followed by expansion culture to obtain a seed liquid; and then inoculating the seed liquid into the fermentation medium for fermentation.

The seed liquid is prepared according to a method conventionally used in the art. Preferably, the seed liquid is prepared through steps of (1) activating the *Mortierellaalpina* strain to obtain a spore suspension;
(2) inoculating the spore suspension into a seed culture medium followed by shake flask expansion culture to obtain a primary seed liquid; and
(3) inoculating the primary seed liquid obtained in step (2) into an expansion culture medium followed by seed tank expansion culture to obtain the target seed liquid.

The spore suspension provided herein can be prepared by one or more activations.

The activation is performed at 25-30° C. for 4-7 days.

Preferably, in step (1), the activating process includes the following steps:

inoculating the *Mortierellaalpina* strain into a primary activation medium followed by culture at 25-30° C. for 5-7 days to obtain primary activated spores; and inoculating the primary activated spores into a secondary activation medium followed by culture at 25-30° C. for 4-6 days to obtain mature spores and hyphae, and preparing a spore suspension.

The primary activation medium and the secondary activation medium used herein are the medium conventionally used in the art to activate the *Mortierellaalpine* strain. Preferably, the primary activation medium and the secondary activation medium are independently a potato dextrose agar (PDA) solid medium.

The PDA medium used herein is purchased or self-made. Preferably, the PDA medium contains 100-300 g/L of potato and 10-30 g/L of sucrose. For the solid PDA medium, 15-17 g/L of agar is additionally added.

The *Mortierellaalpina* strains are preserved in an ampoule or a glycerin tube.

In some embodiments, the primary activation is performed on a slant medium in a test tube.

In some embodiments, the secondary activation is performed on a slant medium in an eggplant-shaped flask.

In some embodiments, the mature spores and hyphae are washed with water to prepare the spore suspension. Preferably, the water is sterile water.

Preferably, in step (2), the shake flask expansion culture is performed at 25-30° C. for 5-8 days.

Preferably, the seed culture medium includes a carbon source and a nitrogen source. A concentration of the carbon source is 50-70 g/L; a concentration of the nitrogen source is 15-25 g/L; and a pH value of the seed culture medium is 6.5-7.2.

The shake flask expansion culture is performed at 180 r/min on a shaker.

Preferably, in step (3), the primary seed liquid obtained in step (2) is inoculated into the expansion culture medium and then undergoes a seed tank expansion culture to obtain the target seed liquid.

Preferably, the seed tank expansion culture is performed at 27-31° C. for 1-2 days under a ventilation rate of 0.5-0.8 vvm.

Preferably, the expansion culture medium includes a carbon source and a nitrogen source, and a carbon-to-nitrogen ratio is (3-8):1.

In some embodiments, in step (3), the primary seed liquid obtained in step (2) is inoculated into a primary expansion culture medium for primary expansion culture, and then inoculated into a secondary expansion culture medium for secondary expansion culture to obtain the target seed liquid.

Preferably, the primary expansion culture is performed at 27-31° C. for 1-2 days under a ventilation rate of 0.5-0.8 vvm.

Preferably, the secondary expansion culture is performed at 27-31° C. for 1-2 days under a ventilation rate of 0.5-0.8 vvm.

Preferably, the primary expansion culture medium includes a carbon source and a nitrogen source, and a carbon-to-nitrogen ratio is (3-8):1.

Preferably, the secondary expansion culture medium includes a carbon source and a nitrogen source, and a carbon-to-nitrogen ratio is (3-8):1.

The types of carbon sources and nitrogen sources in the various medium used herein refer to the carbon sources and nitrogen sources described in the fermentation medium.

In some embodiments, the target seed liquid is prepared according to the following steps:

(1) inoculating the *Mortierellaalpina* strain into a PDA slant medium followed by culture until spores appear and mature; and preparing a spore suspension;
(2) inoculating the spore suspension obtained in step (1) into a seed culture medium in a shake flask; and
(3) inoculating the culture in the shake flask into a primary seed tank followed by culture for 1-2 days; and inoculating the culture in the primary seed tank into a secondary seed tank followed by culture for 1-2 days to obtain the target seed liquid.

Preferably, in the step (1), the *Mortierellaalpina* strain is inoculated onto the PDA slant medium in a test tube, and cultured at 25-30° C. for 5-7 days for the growth of the spores; then the spores are inoculated into a PDA slant medium in an eggplant-shaped flask, and cultured at 25-30° ° C. for 4-6 days to allow the spores to mature. Hyphae and the spores on the PDA slant medium are collected and prepared into the spore suspension with sterile water.

Preferably, in the step (2), the spore suspension obtained in step (1) is inoculated into the seed culture medium in the shake flask, and cultured at 25-30° C. and 180-200 r/min for 3-6 days, where the seed culture medium contains 50-70 g/L of the carbon source and 15-25 g/L of the nitrogen source, and has a pH of 6.8-7.2. Specifically, the spores in each eggplant-shaped flask are inoculated into 2-3 shake flasks, and volumes of the eggplant-shaped flask and the shake flask are both 500 mL.

Specifically, in the step (3), the culture in the primary seed tank is performed at 27-31° C. for 1-2 days, where a ventilation rate is 0.5-0.8 vvm and a carbon-to-nitrogen ratio is (3-8):1, and then the culture in the secondary seed tank is performed at 27-31° ° C. for 1-2 days, where a ventilation rate is 0.5-0.8 vvm and a carbon-to-nitrogen ratio is (3-8):1.

The present disclosure may further process the above-mentioned fermentation product to obtain a microbial oil. There are no special requirements for the processing method as long as the method can extract the microbial oil from the fermentation product. In order to improve the production of the microbial oil, the fermentation product is subjected to extraction.

In a third aspect, the present disclosure provides a microbial oil produced by the method mentioned above. The microbial oil includes a triglyceride, and Sn-2 fatty acids of the triglyceride include 23% or more by weight of ARA.

Preferably, a weight percentage of ARA in the microbial oil is not less than 38%.

In a fourth aspect, the present disclosure further provides a food including the microbial oil mentioned above.

Preferably, the food is an infant formula food, a nutraceutical or a health food.

In a fifth aspect, the present disclosure provides a *Mortierellaalpina* strain, where the *Mortierellaalpina* strain has an accession number of GDMCC No. 60734.

The method for obtaining the *Mortierellaalpina* strain has been described in the second aspect, and will not be repeated here.

In a sixth aspect, the present disclosure provides a use of the *Mortierellaalpina* strain in the production of the microbial oil.

Preferably, the microbial oil includes a triglyceride, and Sn-2 fatty acids of the triglyceride include 23% or more by weight of ARA.

Preferably, a weight percentage of ARA in the microbial oil is not less than 38%.

The present disclosure will be further described in detail below with reference to the embodiments.

In the embodiments, a content of ARA in a microbial oil is detected according to GB 26401-2011; and a fatty acid composition of the microbial oil is detected according to GB 5009. 168-2016.

The absorption rate of ARA in human body is evaluated by an efficacy trial, where male and female subjects are required to take in the microbial oil produced by the method of the present disclosure and a control microbial oil produced by an ordinary *Mortierellaalpina* strain, and then blood samples are collected to determine a content of the Sn-2 ARA in the blood to calculate the absorption rate of ARA.

The ordinary *Mortierella alpina* strain is provided by China Center of Industrial Culture Collection, and has an accession number of CICC 11092s.

The glucose, starch, yeast powder, yeast extract, peptone, a corn steep liquor powder, potatoes and agar are all commercially available.

The PDA culture medium used herein contains 200 g of potatoes, 20 g of sucrose, 15-17 g of agar and 1000 mL of water.

The method provided herein for producing microbial oil by fermentation using *Mortierellaalpine* will be specifically described in Examples 1-3.

PREPARATION EXAMPLE

Preparation of *Mortierellaalpina* Strain (GDMCC No. 60734)

A parent strain preserved in the ampoule inoculated onto a PDA slant medium and cultured at 27° C. for 5 days. The grown spores were transferred to another PDA slant medium and cultured at 27° C. for 4 days to be mature. The mature spores were washed off with 20 mL of sterile water to prepare a spore suspension, and a concentration of the spore suspension was adjusted to $10^6$-$10^8$ spores/mL.

1 μL of the spore suspension was spread to a sterilized sample slide, and was subjected to ARTP mutagenesis in a multifunctional mutagenesis system (MPMS) produced by Adhoc Interteck Co., Ltd. (Beijing, China), where the ARTP mutagenesis was carried out at a plasma mutagenesis power of 100 W, a gas flow rate of 10 SLM and a treatment distance of 2 mm for 25 s, and a lethality rate was 93.33%. Well-grown single colonies were selected for passage, and then inoculated into a shake flask containing the PDA medium and cultured at 27° C. for 4 days. A preliminary screening was performed to detect a content of the Sn-2 position ARA in the culture to select high-yield strains. The high-yield strains obtained by the preliminary screening were subjected to secondary screening by culture in a shake flask at 27° ° C. for 4 days to further select high-yield strains. The genetic stability of the high-yield strains obtained by the secondary screening was investigated. After 5 passages, the strain with stable genetic traits was used as the production strain and stored for long-term use.

After screening, the *Mortierellaalpina* strain GDMCC No. 60734 of the present disclosure was obtained, which had been deposited in Guangdong Microbial Culture Collection Center (GDMCC, Guangdong Institute of Microbiology, 5th Floor, No. 59 Building, No. 100 Xianliezhong Road, Guangzhou, 510070, China) on Aug. 8, 2019.

Example 1

Preparation of a Microbial Oil by Fermentation Using the *Mortierellaalpine* Strain GDMCC No. 60734

(1) An ordinary *Mortierellaalpine* strain and the *Mortierellaalpine* strain GDMCC No. 60734 used herein were inoculated onto a PDA slant medium in a test tube, respectively, and cultured at 27° C. for 5 days. The grown spores were inoculated into a PDA slant medium in an eggplant-shaped flask, and cultured at 27° C. for 4 days to become mature. The hyphae and the spores on the medium were washed off with 20 mL of sterile water to prepare a spore suspension.

(2) The spore suspension obtained in step (1) was inoculated into a seed culture medium in a shake flask, and cultured at 27° C. and 180 r/min on a shaker for 4 days, where the spore suspension in each eggplant-shaped flask was inoculated into 2-3 shake flasks, and the seed culture medium contained 50 g/L of glucose and 15 g/L of yeast powder, and had a pH of 7.2.

(3) 1 L of the culture in the shake flasks was inoculated in a 1 $m^3$ primary seed tank containing 500 L of a primary expansion culture medium, and cultured at 29° C. and 180 r/min under a ventilation rate of 0.65 vvm for 2 days, where the primary expansion culture medium contained 30 g/L of glucose and 15 g/L of yeast extract, and had a pH of 7.2.

(4) 500 L of the culture product in the primary seed tank obtained in step (3) was inoculated in a 10 $m^3$ secondary seed tank containing 7 $m^3$ of a secondary expansion culture medium, and cultured at 29° C. and 120 r/min under a ventilation rate of 0.65 vvm for 2 days, where the secondary expansion culture medium contained 30 g/L of glucose and 15 g/L of yeast extract, and had a pH of 7.2. A seed liquid was obtained when a concentration of the hyphae reached 3.5%, and then transferred to a fermentation tank.

(5) 2 $m^3$ of the seed liquid obtained in step (4) was inoculated into a 45 $m^3$ fermentation tank containing 22 $m^3$ of a fermentation medium, and cultured at 29° C. and 90 r/min under a ventilation rate of 0.9 vvm for 6 days to obtain a fermentation product, where the carbon-nitrogen ratio was controlled at (8-16):1 by adding a sterile glucose solution (250 g/L) during the fermentation, and the fermentation medium contained 30 g/L of sucrose and 15 g/L of yeast extract, and had a pH of 7.5.

(6) The fermentation product obtained in step (5) was separated to obtain wet cells, which were dried and subjected to extraction with hexane to obtain an oil. The solid phase separated after extraction was transferred to an extraction vessel for repeated extraction 4-7 times, and the oil remaining in the residue after extractions was controlled to be less than 7%. A weight ratio of the solvent to the dried cell during the extraction was 1.5:1. The oil phases obtained by filtration and separation after each extraction were combined and desolventized to obtain a microbial oil.

(7) The microbial oil obtained in step (6) was detected to obtain a content of ARA, a fatty acid composition and a weight percentage of ARA at the Sn-2 position of triglyceride in the microbial oil, and the results were shown in Table 1.

TABLE 1

Parameters of the microbial oils in Example 1

| | Ordinary *Mortierellaalpina* strain | *Mortierellaalpina* GDMCC No. 60734 |
|---|---|---|
| ARA (C20:4), g/100 g | 40.71 | 44.067 |
| Palmitic acid (C16:0), g/100 g | 7.356 | 7.274 |
| Stearic acid (C18:0), g/100 g | 6.825 | 6.714 |
| Oleic acid (C18:1), g/100 g | 6.013 | 5.924 |
| Linoleic acid (C18:2), g/100 g | 5.922 | 6.044 |
| Weight percentage of ARA at the Sn-2 position of triglyceride, % | 21.97 | 32.65 |
| Weight percentage of ARA at Sn-1 and Sn-3 positions of triglyceride, % | 56.15 | 52.8 |
| Absorption rate of ARA, % | 46.7 | 65.7 |

Example 2

Preparation of a Microbial Oil by Fermentation Using the *Mortierellaalpine* Strain GDMCC No. 60734

(1) An ordinary *Mortierellaalpine* strain and the *Mortierellaalpine* strain GDMCC No. 60734 used herein were inoculated onto a PDA slant medium in a test tube, respectively, and cultured at 28° C. for 6 days. The grown spores were inoculated into a PDA slant medium in an eggplant-shaped flask, and cultured at 28° C. for 5 days to become mature. The hyphae and the spores on the medium were washed off with 20 mL of sterile water to prepare a spore suspension.

(2) The spore suspension obtained in step (1) was inoculated into a seed culture medium in a shake flask, and cultured at 28° ° C. and 200 r/min on a shaker for 5 days, where the spore suspension in each eggplant-shaped flask was inoculated into 2-3 shake flasks, and the seed culture medium contained 60 g/L of glucose, 10 g/L of yeast powder and 10 g/L of peptone, and had a pH of 7.0.

(3) 200 mL of the culture in the shake flasks was inoculated into a 5 L seed tank containing 3 L of an expansion culture medium, and cultured at 28° C. and 200 r/min under a ventilation rate of 0.6 vvm for 1 day to obtain a seed liquid, where the expansion culture medium contained 35 g/L of glucose and 20 g/L of yeast powder, and had a pH of 7.2.

(4) 1.5 L of the seed liquid obtained in step (3) was inoculated into a 30 L fermentation tank containing 15 L of a fermentation medium, and cultured at 28° C. and 220 r/min under a ventilation rate of 0.8 vvm for 7 days to obtain a fermentation product, where the carbon-nitrogen ratio was controlled at (5-12):1 by adding a sterile glucose solution (250 g/L) during the fermentation, and the fermentation medium contained 50 g/L of glucose, 10 g/L of starch and 20 g/L of yeast extract, and had a pH of 8.

(5) The fermentation product obtained in step (4) was separated to obtain wet cells, which were dried and subjected to extraction with hexane to obtain an oil. The solid phase separated after extraction was transferred to an extraction vessel for repeated extraction 4-7 times, and the oil remaining in the residue after extractions was controlled to be less than 7%. A weight ratio of the solvent to the dried cell during the extraction was 1.5:1. The oil phases obtained by filtration and separation after each extraction were combined and desolventized to obtain a microbial oil.

(6) The microbial oil obtained in step (5) was detected to obtain a content of ARA, a fatty acid composition and a weight percentage of ARA at the Sn-2 position of triglyceride in the microbial oil, and the results were shown in Table 2.

TABLE 2

Parameters of the microbial oils in Example 2

| | Ordinary *Mortierellaalpina* strain | *Mortierellaalpina* GDMCC No. 60734 |
|---|---|---|
| ARA (C20:4), g/100 g | 39.36 | 43.18 |
| Palmitic acid (C16:0), g/100 g | 8.541 | 7.236 |
| Stearic acid (C18:0), g/100 g | 7.136 | 6.696 |
| Oleic acid (C18:1), g/100 g | 6.132 | 5.891 |
| Linoleic acid (C18:2), g/100 g | 5.879 | 6.007 |
| Weight percentage of ARA at Sn-2 position of triglyceride, % | 20.97 | 32.17 |
| Weight percentage of ARA at Sn-1 and Sn-3 positions of triglyceride, % | 57.83 | 51.4 |
| Absorption rate of ARA, % | 43.8 | 62.1 |

Example 3

Preparation of a Microbial Oil by Fermentation Using the *Mortierellaalpine* Strain GDMCC No. 60734

(1) An ordinary *Mortierellaalpine* strain and the *Mortierellaalpine* strain GDMCC No. 60734 used herein were inoculated onto a PDA slant medium in a test tube, respectively, and cultured at 29° C. for 7 days. The grown spores were inoculated into a PDA slant medium in an eggplant-shaped flask, and cultured at 29° C. for 6 days to become mature. The hyphae and the spores on the medium were washed off with 20 mL of sterile water to prepare a spore suspension.

(2) The spore suspension obtained in step (1) was inoculated into a seed culture medium in a shake flask, and cultured at 29° C. and 190 r/min on a shaker for 6 days, where the spore suspension in each eggplant-shaped flask was inoculated into 2-3 shake flasks, and the seed culture medium contained 60 g/L of glucose, 25 g/L of yeast powder and 10 g/L of starch, and had a pH of 7.2.

(3) 300 mL of the culture in the shake flasks was inoculated into a 10 L seed tank containing 6 L of an expansion culture medium, and cultured at 30° C. and 220 r/min under a ventilation rate of 0.75 vvm for 2 days to obtain a seed liquid, where the expansion culture medium contained 40 g/L of glucose and 25 g/L of yeast powder, and had a pH of 6.8.

(4) 2.75 L of the seed liquid obtained in step (3) was inoculated into a 100 L fermentation tank containing 55 L of a fermentation medium, and cultured at 30° C. and 200 r/min under a ventilation rate of 0.85 vvm for 5 days to obtain a fermentation product, where the carbon-nitrogen ratio was controlled at (3-10):1 by adding a sterile glucose solution (250 g/L) during the fermentation, and the fermentation medium contained 45 g/L of glucose, 10 g/L of corn steep liquor powder and 10 g/L of peptone, and had a pH of 7.0.

(5) The fermentation product obtained in step (4) was separated to obtain wet cells, which were dried and subjected to extraction with hexane to obtain an oil. The solid phase separated after extraction was transferred to an extraction vessel for repeated extraction 4-7 times, and the oil remaining in the residue after extractions was controlled to be less than 7%. A weight ratio of the solvent to the dried cell during the extraction was 1.5:1. The oil phases obtained by filtration and separation after each extraction were combined and desolventized to obtain a microbial oil.

(6) The microbial oil obtained in step (5) was detected to obtain a content of ARA, a fatty acid composition and a weight percentage of ARA at the Sn-2 position of triglyceride in the microbial oil, and the results were shown in Table 3.

TABLE 3

Parameters of the microbial oils in Example 3

| | Ordinary *Mortierellaalpina* strain | *Mortierellaalpina* GDMCC No. 60734 |
|---|---|---|
| ARA (C20:4), g/100 g | 38.73 | 41.17 |
| Palmitic acid (C16:0), g/100 g | 8.136 | 7.257 |
| Stearic acid (C18:0), g/100 g | 7.167 | 6.721 |
| Oleic acid (C18:1), g/100 g | 6.939 | 5.916 |
| Linoleic acid (C18:2), g/100 g | 6.871 | 6.009 |
| Weight percentage of ARA at Sn-2 position of triglyceride, % | 20.15 | 31.98 |
| Weight percentage of ARA at Sn-1 and Sn-3 positions of triglyceride, % | 56.91 | 52.31 |
| Absorption rate of ARA, % | 42.1 | 63.1 |

The above-mentioned embodiments are only preferred embodiments of the disclosure, and are not intended to limit the scope of the present disclosure. It should be noted that variations and modifications made by those of ordinary skill in the art without departing from the spirit of the disclosure should fall within the scope of the present disclosure.

What is claimed is:

1. A method for producing a microbial oil, comprising:

performing an atmospheric room temperature plasma (ARTP) mutagenesis on spores of a starting strain in a form of a spore suspension for 1-6 min at a plasma mutagenesis power of 80-120 W, a gas flow rate of 8-12 SLM (standard liter per minute) and a treatment distance of 1-3 mm, followed by screening so as to obtain a *Mortierellaalpina* strain; wherein a concentration of the spore suspension is $10^6$-$10^8$ spores/mL;

inoculating the *Mortierellaalpina* strain into a fermentation medium for fermentation to obtain a fermentation product; and subjecting the fermentation product to extraction to produce the microbial oil;

wherein the fermentation is performed at 27-31° C. for 4-8 days under a ventilation rate of 0.5-1.1 vvm; and the fermentation medium comprises a carbon source and a nitrogen source, and has a carbon-to-nitrogen ratio of (3-18):1.

2. The method according to claim 1, further comprising:

activating the *Mortierellaalpina* strain followed by expansion culture to produce a seed liquid; and inoculating the seed liquid into the fermentation medium for the fermentation;

wherein the seed liquid is obtained through steps of:

(1) activating the *Mortierellaalpina* strain to obtain a spore suspension;

(2) inoculating the spore suspension obtained in step (1) into a seed culture medium in a shake flask for primary expansion culture; and (3) inoculating a culture product in the shake flask into an expansion culture medium in a seed tank for secondary expansion culture to obtain the seed liquid;

the step (1) further comprises:

inoculating the *Mortierellaalpina* strain into a primary activation medium, and culturing the *Mortierellaalpina* strain at 25-30° C. for 5-7 days to obtain primary activated spores;

inoculating the primary activated spores into a secondary activation medium, and culturing the primary activated spores at 25-30° C. for 4-6 days to obtain mature spores and hyphae; and preparing the spore suspension;

in the step (2), the primary expansion culture is performed at 25-30° ° C. for 5-8 days; and in the step (3), the secondary expansion culture is performed at 27-31° C. for 1-2 days under a ventilation rate of 0.5-0.8 vvm.

3. The method according to claim 2, wherein the seed culture medium in the shake flask comprises 50-70 g/L of a carbon source and 15-25 g/L of a nitrogen source, and has a pH of 6.5-7.2; and the expansion culture medium comprises a carbon source and a nitrogen source, and has a carbon-to-nitrogen ratio of (3-8):1.

4. The method according to claim 3, wherein the carbon source in the fermentation medium, the carbon source in the seed culture medium and the carbon source in the expansion culture medium are independently selected from the group consisting of glucose, starch and a combination thereof; and the nitrogen source in the fermentation medium, the nitrogen source in the seed culture medium and the nitrogen source in the expansion culture medium are independently selected from the group consisting of peptone, yeast powder, yeast extract, a corn steep liquor powder and a combination thereof.

5. A method of producing a microbial oil using a *Mortierellaalpina* strain, comprising:

performing an atmospheric room temperature plasma (ARTP) mutagenesis on spores of a starting strain in a form of a spore suspension for 1-6 min at a plasma mutagenesis power of 80-120 W, a gas flow rate of 8-12 SLM (standard liter per minute) and a treatment distance of 1-3 mm, followed by screening so as to obtain the *Mortierellaalpina* strain; wherein a concentration of the spore suspension is $10^6$-$10^8$ spores/mL;

inoculating the *Mortierellaalpina* strain into a fermentation medium for fermentation to produce the microbial oil;

wherein the *Mortierellaalpina* strain has an accession number of GDMCC No. 60734; the microbial oil comprises a triglyceride; Sn-2 fatty acids of the triglyceride comprise 23% or more by weight of arachidonic acid; and a weight percentage of arachidonic acid in the microbial oil is not less than 38% by weight of the microbial oil.

* * * * *